(12) United States Patent
Alberghina et al.

(10) Patent No.: US 8,401,615 B1
(45) Date of Patent: Mar. 19, 2013

(54) PLANAR COIL FLEXION FIXTURE FOR MAGNETIC RESONANCE IMAGING AND USE THEREOF

(75) Inventors: John Alberghina, East Northport, NY (US); Jevan Damadian, East Northport, NY (US)

(73) Assignee: Fonar Corporation, Melville, NY (US)

( * ) Notice: Subject to any disclaimer, the term of this patent is extended or adjusted under 35 U.S.C. 154(b) by 1221 days.

(21) Appl. No.: 10/987,822

(22) Filed: Nov. 12, 2004

(51) Int. Cl.
*A61B 5/05* (2006.01)

(52) U.S. Cl. .............. 600/415; 600/422; 5/601; 5/621; 324/318

(58) Field of Classification Search .............. 600/410, 600/415, 422, 411, 427; 324/318, 322, 307, 324/309; 5/601, 610, 611, 621–624
See application file for complete search history.

(56) References Cited

U.S. PATENT DOCUMENTS

| | | | |
|---|---|---|---|
| 3,810,254 A | 5/1974 | Utsumi et al. |
| 4,407,292 A | 10/1983 | Edrich |
| 4,411,270 A | 10/1983 | Damadian |
| 4,534,076 A | 8/1985 | Barge |
| 4,534,358 A | 8/1985 | Young |
| D283,858 S | 5/1986 | Opsvik |
| 4,608,991 A | 9/1986 | Rollwitz |
| 4,613,820 A | 9/1986 | Edelstein et al. |
| 4,614,378 A | 9/1986 | Picou |
| 4,629,989 A | 12/1986 | Riehl et al. |
| 4,641,119 A | 2/1987 | Moore |
| 4,644,275 A | 2/1987 | Young |
| 4,651,099 A | 3/1987 | Vinegar et al. |
| 4,663,592 A | 5/1987 | Yamaguchi et al. |
| 4,668,915 A | 5/1987 | Daubin et al. |
| 4,672,346 A | 6/1987 | Miyamoto et al. |
| 4,675,609 A | 6/1987 | Danby et al. |
| 4,679,022 A | 7/1987 | Miyamoto et al. |
| 4,707,663 A | 11/1987 | Minkoff et al. |
| 4,766,378 A | 8/1988 | Danby et al. |
| 4,767,160 A | 8/1988 | Mengshoel et al. |
| 4,770,182 A | 9/1988 | Damadian et al. |
| 4,777,464 A | 10/1988 | Takabatashi et al. |
| 4,816,765 A | 3/1989 | Boskamp |
| 4,829,252 A | 5/1989 | Kaufman |
| 4,866,387 A | 9/1989 | Hyde et al. |
| 4,875,485 A | 10/1989 | Matsutani |
| 4,908,844 A | 3/1990 | Hasegawa |
| 4,918,388 A | 4/1990 | Mehdizadeh et al. |

(Continued)

FOREIGN PATENT DOCUMENTS

| | | |
|---|---|---|
| DE | 3140 225 | 10/1981 |
| JP | 1242056 | 9/1989 |

(Continued)

OTHER PUBLICATIONS

U.S. Appl. No. 10/419,385.

(Continued)

*Primary Examiner* — Elmer Chao
(74) *Attorney, Agent, or Firm* — Lerner, David, Littenberg, Krumholz & Mentlik, LLP

(57) ABSTRACT

An aspect of the present invention is a system for magnetic resonance imaging that includes a fixture for housing an antenna such that the position of a portion of a patient's anatomy remains fixed relative to the antenna as the patient moves between a first and a second position for imaging.

28 Claims, 14 Drawing Sheets

U.S. PATENT DOCUMENTS

| | | | |
|---|---|---|---|
| 4,920,318 A | 4/1990 | Misic et al. |
| 4,924,198 A | 5/1990 | Laskaris |
| 4,943,774 A | 7/1990 | Breneman et al. |
| 4,968,937 A | 11/1990 | Akgun |
| D313,073 S | 12/1990 | Kaufman et al. |
| 4,985,678 A | 1/1991 | Gangarosa et al. |
| 5,008,624 A | 4/1991 | Yoshida |
| 5,030,915 A | 7/1991 | Boskamp et al. |
| 5,050,605 A | 9/1991 | Eydelman et al. |
| 5,061,897 A | 10/1991 | Danby et al. |
| 5,062,415 A | 11/1991 | Weatherby et al. |
| 5,065,761 A | 11/1991 | Pell |
| 5,081,665 A | 1/1992 | Kostich |
| 5,085,219 A | 2/1992 | Ortendahl et al. |
| 5,124,651 A | 6/1992 | Danby et al. |
| 5,134,374 A | 7/1992 | Breneman et al. |
| 5,153,517 A | 10/1992 | Oppelt et al. |
| 5,153,546 A | 10/1992 | Laskaris |
| 5,155,758 A | 10/1992 | Vogl |
| 5,162,768 A | 11/1992 | McDougall et al. |
| 5,171,296 A | 12/1992 | Herman |
| 5,194,810 A | 3/1993 | Breneman et al. |
| 5,197,474 A | 3/1993 | Englund et al. |
| 5,207,224 A | 5/1993 | Dickinson et al. |
| 5,211,165 A | 5/1993 | Dumoulin et al. |
| 5,221,902 A | 6/1993 | Jones et al. |
| 5,229,723 A | 7/1993 | Sakurai et al. |
| 5,250,901 A | 10/1993 | Kaufman et al. |
| 5,251,961 A | 10/1993 | Pass |
| 5,256,971 A | 10/1993 | Boskamp |
| 5,274,332 A | 12/1993 | Jaskolski et al. |
| 5,277,183 A | 1/1994 | Vij |
| 5,291,890 A | 3/1994 | Cline et al. |
| 5,293,519 A | 3/1994 | Yoshino et al. |
| 5,304,932 A | 4/1994 | Carlson |
| 5,305,365 A | 4/1994 | Coe |
| 5,305,749 A | 4/1994 | Li et al. |
| 5,315,244 A | 5/1994 | Griebeler |
| 5,315,276 A | 5/1994 | Huson et al. |
| 5,317,297 A | 5/1994 | Kaufman et al. |
| 5,323,113 A | 6/1994 | Cory et al. |
| 5,349,956 A | 9/1994 | Bonutti |
| 5,361,764 A | 11/1994 | Reynolds et al. |
| 5,378,988 A | 1/1995 | Pulyer |
| 5,382,904 A | 1/1995 | Pissanetzky |
| 5,382,905 A | 1/1995 | Miyata et al. |
| 5,386,447 A | 1/1995 | Siczek |
| 5,394,087 A | 2/1995 | Molyneaux |
| 5,412,363 A | 5/1995 | Breneman et al. |
| 5,436,607 A | 7/1995 | Chari et al. |
| 5,471,142 A | 11/1995 | Wang |
| 5,473,251 A | 12/1995 | Mori |
| 5,475,885 A | 12/1995 | Ishikawa |
| 5,477,146 A | 12/1995 | Jones |
| 5,490,513 A | 2/1996 | Damadian et al. |
| 5,515,863 A | 5/1996 | Damadian |
| 5,519,372 A | 5/1996 | Palkovich et al. |
| 5,548,218 A | 8/1996 | Lu |
| 5,553,777 A | 9/1996 | Lampe |
| 5,566,681 A | 10/1996 | Manwaring et al. |
| 5,578,925 A | 11/1996 | Molyneaux et al. |
| 5,592,090 A | 1/1997 | Pissanetzky |
| 5,602,479 A | 2/1997 | Srinivasan et al. |
| 5,606,970 A | 3/1997 | Damadian |
| 5,621,323 A | 4/1997 | Larsen |
| 5,623,241 A | 4/1997 | Minkoff |
| 5,640,958 A | 6/1997 | Bonutti |
| 5,652,517 A | 7/1997 | Maki et al. |
| 5,654,603 A | 8/1997 | Sung et al. |
| 5,666,056 A | 9/1997 | Cuppen et al. |
| 5,671,526 A | 9/1997 | Merlano |
| 5,680,861 A | 10/1997 | Rohling |
| 5,682,098 A | 10/1997 | Vij |
| 5,735,278 A | 4/1998 | Hoult et al. |
| 5,743,264 A | 4/1998 | Bonutti |
| 5,754,085 A | 5/1998 | Danby et al. |
| 5,779,637 A | 7/1998 | Palkovich et al. |
| 5,836,878 A | 11/1998 | Mock et al. |
| 5,845,220 A | 12/1998 | Puthoff |
| 5,862,579 A | 1/1999 | Blumberg |
| 5,929,639 A | 7/1999 | Doty |
| 5,951,474 A | 9/1999 | Matsunaga et al. |
| D417,085 S | 11/1999 | Kanwetz, II |
| 5,983,424 A | 11/1999 | Naslund |
| 5,988,173 A | 11/1999 | Scruggs |
| 6,008,649 A | 12/1999 | Boskamp et al. |
| 6,011,396 A | 1/2000 | Eckels et al. |
| 6,014,070 A | 1/2000 | Danby et al. |
| 6,023,165 A | 2/2000 | Damadian et al. |
| 6,029,082 A | 2/2000 | Srinivasan et al. |
| 6,075,364 A | 6/2000 | Damadian et al. |
| 6,094,116 A | 7/2000 | Tai et al. |
| 6,122,541 A | 9/2000 | Cosman et al. |
| 6,137,291 A | 10/2000 | Szumowski et al. |
| 6,138,302 A | 10/2000 | Sashin et al. |
| 6,141,579 A | 10/2000 | Bonutti |
| 6,144,203 A | 11/2000 | Richard et al. |
| 6,144,204 A | 11/2000 | Sementchenko |
| 6,150,819 A | 11/2000 | Laskaris et al. |
| 6,150,820 A | 11/2000 | Damadian et al. |
| 6,201,394 B1 | 3/2001 | Danby et al. |
| 6,208,144 B1 | 3/2001 | McGinley et al. |
| 6,226,856 B1 | 5/2001 | Kazama et al. |
| 6,246,239 B1 | 6/2001 | Krogmann et al. |
| 6,246,900 B1 | 6/2001 | Cosman et al. |
| 6,249,121 B1 | 6/2001 | Boskamp et al. |
| 6,249,695 B1 | 6/2001 | Damadian |
| 6,285,188 B1 | 9/2001 | Sakakura |
| 6,344,745 B1 | 2/2002 | Reisker et al. |
| 6,346,814 B1 | 2/2002 | Carrozzi et al. |
| 6,357,066 B1 | 3/2002 | Pierce |
| 6,369,571 B1 | 4/2002 | Damadian et al. |
| 6,377,044 B1 | 4/2002 | Burl et al. |
| 6,377,836 B1 | 4/2002 | Arakawa et al. |
| 6,385,481 B2 | 5/2002 | Nose et al. |
| 6,404,199 B1 | 6/2002 | Fujita et al. |
| 6,411,088 B1 | 6/2002 | Kuth et al. |
| 6,414,490 B1 | 7/2002 | Damadian et al. |
| 6,424,854 B2 | 7/2002 | Hayashi et al. |
| 6,456,075 B1 | 9/2002 | Damadian et al. |
| 6,504,371 B1 | 1/2003 | Damadian et al. |
| 6,515,479 B1 | 2/2003 | Arz et al. |
| 6,549,800 B1 | 4/2003 | Atalar et al. |
| 6,591,128 B1 | 7/2003 | Wu et al. |
| 6,639,406 B1 | 10/2003 | Boskamp et al. |
| 6,650,926 B1 * | 11/2003 | Chan et al. .................... 600/422 |
| 6,677,753 B1 | 1/2004 | Danby et al. |
| 6,697,659 B1 | 2/2004 | Bonutti |
| 6,750,653 B1 | 6/2004 | Zou et al. |
| 6,792,257 B2 | 9/2004 | Rabe |
| 6,801,038 B2 | 10/2004 | Carrozzi et al. |
| 6,806,711 B2 | 10/2004 | Reykowski |
| 6,822,447 B1 | 11/2004 | Yamagata |
| 6,831,460 B2 | 12/2004 | Reisker et al. |
| 6,850,064 B1 | 2/2005 | Srinivasan |
| 6,882,149 B2 | 4/2005 | Nitz et al. |
| 6,882,877 B2 | 4/2005 | Bonutti |
| 6,894,495 B2 | 5/2005 | Kan |
| 6,954,069 B2 | 10/2005 | Harvey et al. |
| 6,980,002 B1 | 12/2005 | Petropoulos et al. |
| 7,002,341 B2 | 2/2006 | Baudenbacher et al. |
| 7,046,006 B2 | 5/2006 | Creemers et al. |
| 7,049,819 B2 | 5/2006 | Chan et al. |
| 7,221,161 B2 | 5/2007 | Fujita et al. |
| 7,245,127 B2 | 7/2007 | Feng et al. |
| 7,348,778 B2 | 3/2008 | Chu et al. |
| 7,474,098 B2 | 1/2009 | King |
| 2001/0029330 A1 | 10/2001 | Nose et al. |
| 2002/0013524 A1 | 1/2002 | Hayashi et al. |
| 2002/0032927 A1 | 3/2002 | Dinkler |
| 2002/0101241 A1 | 8/2002 | Chui |
| 2002/0123681 A1 | 9/2002 | Zuk et al. |
| 2002/0196021 A1 | 12/2002 | Wang |
| 2003/0071622 A1 | 4/2003 | Reisker et al. |
| 2003/0204136 A1 | 10/2003 | Green et al. |

| | | | |
|---|---|---|---|
| 2003/0210049 | A1 | 11/2003 | Boskamp et al. |
| 2004/0030241 | A1* | 2/2004 | Green et al. ............ 600/422 |
| 2004/0220469 | A1 | 11/2004 | Jevtic et al. |

FOREIGN PATENT DOCUMENTS

| | | |
|---|---|---|
| JP | 4-332531 | 11/1992 |
| JP | 62-26052 | 8/1994 |
| JP | 08-050843 | 2/1996 |
| WO | WO-97/17896 | 5/1997 |

OTHER PUBLICATIONS

Four (4) photographs of an exhibit at the Radiological Society for North America held in Dec. 1996.

U.S. Appl. No. 09/718,946, filed Nov. 22, 2000.

Weis et al., Simulation of the influence of magnetic field inhomogeneity and distortion correction in MR imaging, vol. 8, No. 4, p. 483-489, 1990 (Abstract).

U.S. Appl. No. 08/978,084, filed Nov. 25, 1997.

U.S. Appl. No. 10/131,843, filed Apr. 25, 2002.

"The design and construction of high field-uniformity permanent magnet system for MRI" Feng, Z.X.; Jiang, X.H.;Han, S.; Magnetics, IEEE Transactions on vol. 28, Issue 1, Jan. 1992 pp. 641-643.

Guclu et al., A method for Preamplifier-Decoupling Improvement in Quadrature Phased-Array Coils, Journal of Magnetic Resonance Imaging, 19:255-258, 2004.

Feng, et al., A New Phased Array Spine Coil for Vertical Field MRI System, Proc. Intl. Soc. Mag. Reson. Med. 11, 2003.

* cited by examiner

PLANAR COIL FLEXION FIXTURE FOR MAGNETIC RESONANCE IMAGING AND USE THEREOF

BACKGROUND

The present invention relates to magnetic resonance imaging systems, apparatus and procedures and, in particular, to apparatus and procedures for imaging the lower lumbar, pelvic or prostate region of a patient's anatomy.

In magnetic resonance imaging, an object to be imaged as, for example, a body of a human subject, is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the nuclei to "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are a dominant factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Many conventional magnetic resonance imaging instruments require that a patient lie on a horizontal bed that is then advanced into a tubular bore within a super-conducting solenoidal magnet used to generate the static magnetic field. Other conventional MRI imaging instruments use a magnet having a ferromagnetic frame defining a patient-receiving space. Considerable effort has been devoted to design of such magnets in a manner which provides a relatively open patient-receiving space, as opposed to the claustrophobic tubular bore of the conventional solenoidal magnet. However, in these instruments as well, it has been the common practice to provide the patient on a bed which remains horizontal throughout the procedure.

Advancement in magnetic resonance imaging has resulted in imaging apparatus that supports a patient in any position between a vertical position and a horizontal position. As described in greater detail in commonly assigned U.S. Pat. Nos. 6,414,490 and 6,677,753, the disclosures of which are hereby incorporated by reference herein, a magnetic resonance imaging system can be provided with a patient support, such as a table, which can extend in a generally vertical direction so that the long axis of the patient is substantially vertical. For example, the patient may be in a standing posture, with his back, side or front leaning against a generally vertical patient support. Such a support may include a footrest projecting from the table at its lower end and the patient may stand on the footrest. In other arrangements, the support includes a seat projecting from the table so that the seat is in a horizontal plane when the table surface is vertical. In particularly preferred arrangements, the patient support can move relative to the magnet. For example, the patient support may be arranged to move vertically relative to the magnet so as to elevate a portion of the patient into the patient-receiving space of the magnet. Alternatively or additionally, the patient support may be arranged to tilt through a range of orientations between a generally horizontal orientation and a generally vertical orientation.

The position of a patient during magnetic resonance imaging may affect or limit the imaging information obtained. A patient may exhibit a symptom if oriented in an upright or weight bearing position and no symptom if oriented in a recumbent or horizontal position. For example, it may be necessary to image a patient in an upright or gravity bearing position to discern a symptom and provide a diagnosis for injuries relating to, for example, the neck, spine, hip, knee, foot or ankle areas of the anatomy.

In addition, dynamic-kinetic imaging of a portion of a patient's anatomy, e.g., the spine, joints or even soft tissue, in different positions, e.g., from a relaxed or resting position to an un-relaxed or flexed position, may yield additional information potentially important to diagnosis. However, when a patient changes position, imaging may be affected due to the change in position of the anatomical area of interest relative to the antenna for receiving magnetic resonance signals.

Of utility then are methods, apparatus and systems for imaging a portion of patient's anatomy in different relative positions having little or no effect on the image or the signals received by the receiving antenna.

SUMMARY OF THE INVENTION

An aspect of the present invention is a system for magnetic resonance imaging. The system preferably comprises a magnetic resonance imaging apparatus having a receiving space for positioning a patient and a patient support device for receiving the patient and that is positionable in the receiving space. The system further preferably includes a fixture for housing an antenna such that the position of a portion of the patient's anatomy to be imaged remains substantially fixed relative to the antenna as the patient moves between a first position and a second position.

In accordance with this aspect of the present invention, the fixture is preferably mounted to the patient support and the portion of the patient's anatomy to be imaged comprises the lumbar spine. Preferably, the first position of the patient may be an upright lumbar position and the second position of the patient may be a flexion lumbar position. In addition, the patient may be oriented in an extended lumbar position and an extension, i.e., arched, lumbar position.

Further in accordance with this aspect of the present invention, the fixture preferably comprises a base portion and an antenna receiving portion pivotably mounted to the base portion. The base portion is preferably mounted to the patient support so as to allow an antenna positioned in the antenna receiving portion to remain fixed relative to the patient's lumbar spine.

The antenna is preferably connectable to a strap worn by the patient, such that as the patient moves between positions, the antenna translates linearly in the antenna receiving portion. The antenna receiving portion may include one or more slots for receiving the strap.

Additionally, the base portion may be pivotably mounted to the antenna receiving portion by a pair of torsional spring members. Further still, the pair of torsional spring members is preferably made from a magnetically translucent material, such as copper, phosphor bronze or 300 series stainless steel.

Further in accordance with this aspect of the present invention, the patient may be positioned in a sitting or standing position.

Another aspect of the present invention is a method for performing magnetic resonance imaging. The method preferably comprises providing a magnetic resonance imaging apparatus having a patient receiving space and patient support device located within the patient receiving space; mounting a fixture to the patient support device; and positioning a patient in the patient receiving space such that the patient's anterior surface is adjacent to the fixture. The method may further desirably comprise acquiring magnetic resonance images of a portion of the patient's anatomy with the patient oriented in a first position and a second position such that the position of the patient's anterior surface remains fixed relative to the fixture during movement between the first and second portions.

Further in accordance with this aspect of the present invention, positioning the patient comprises positioning the patient in a sitting or standing position. In addition, in the first position, the patient's lumbar region may be positioned adjacent to the fixture and oriented in an extended position or in a neutrally upright position. The patient may also be oriented in an extension position.

Further in accordance with this aspect of the present invention, in the second position the patient's lumbar region may be positioned adjacent to the fixture and oriented in a flexion position.

In another aspect, the present invention is a method for performing dynamic kinetic studies of the spine. The method desirably comprises providing magnetic resonance imaging apparatus having a gap and a static horizontal magnetic field within the gap; positioning a patient support device in the gap of the apparatus; equipping the patient support device with a fixture housing a radio frequency coil; positioning the patient next to the patient support device such that a portion of the patient's lumbar region is proximate the fixture; acquiring a first magnetic resonance image of the patient's lumbar region in a first position; orienting the patient in a second position relative to the first position such that the portion of the patient's lumbar region proximate the fixture remains substantially fixed relative to the fixture between the first position and the second position; and acquiring a second magnetic resonance image of the patient's lumbar region in the second position.

In another aspect, the present invention is an apparatus for use in a magnetic resonance imaging system or procedure. The apparatus preferably comprises a base and an antenna holder pivotably mounted to the base such that as a patient moves from a first position to a second position, the position of the patient's anatomy adjacent to an antenna associated with the antenna holder remains substantially fixed relative to the antenna holder.

In accordance with this aspect of the present invention, the antenna holder preferably comprises a base, a pair of sidewalls projecting from the base and a rear wall projecting from the base between the pair of sidewalls to define a slot for holding an antenna. Most preferably, the antenna comprises a planar coil antenna.

Further in accordance with this aspect of the present invention, the antenna holder may comprise a box-like structure having an opening for receiving a planar antenna. The box may be rectangular, square or circular in shape. In general, the box may be of any shape suitable to house the antenna.

Further still in accordance with this aspect of the present invention, the antenna holder is preferably pivotably mounted to the base using a torsional spring.

In another aspect, the present invention is an apparatus for magnetic resonance imaging. The apparatus preferably comprises a base and an antenna for receiving magnetic resonance imaging signals. The apparatus is preferably pivotably mounted to the base about a pivot axis in the base such that as the antenna pivots from a first position to a second position about the pivot axis the antenna translates substantially transverse to an arc defined by the pivoting motion of the antenna about the pivot axis.

Further, in accordance with this aspect of the present invention, the base preferably includes a proximal end and a distal end and wherein the antenna is mounted the proximal end of the base.

In addition, the antenna is mounted using one or more rod members, each rod member having a first end mounted to the proximal end of the base and a second end mounted to the antenna and wherein each of the rod members allow the antenna to translate substantially transverse to an arc defined by the pivoting motion.

DETAILED DESCRIPTION

Figure 1A:
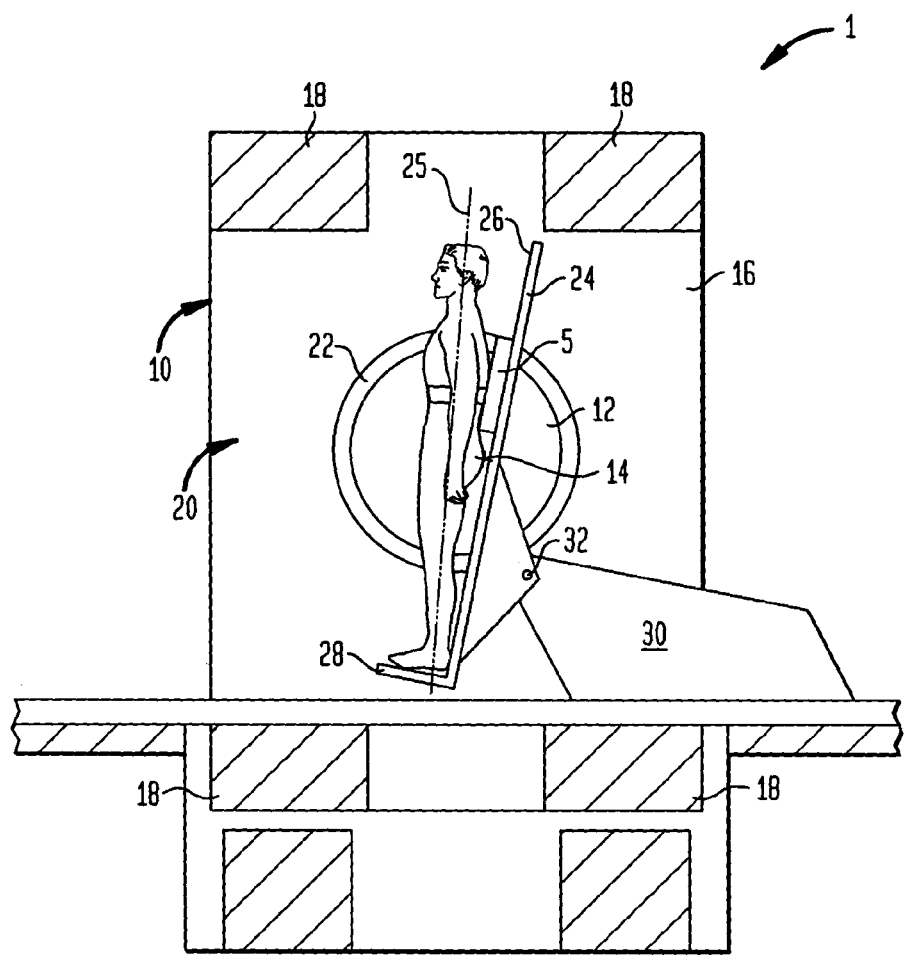
FIG. 1A illustrates a magnetic resonance imaging system in accordance with an aspect of the present invention.
Figure 1B:
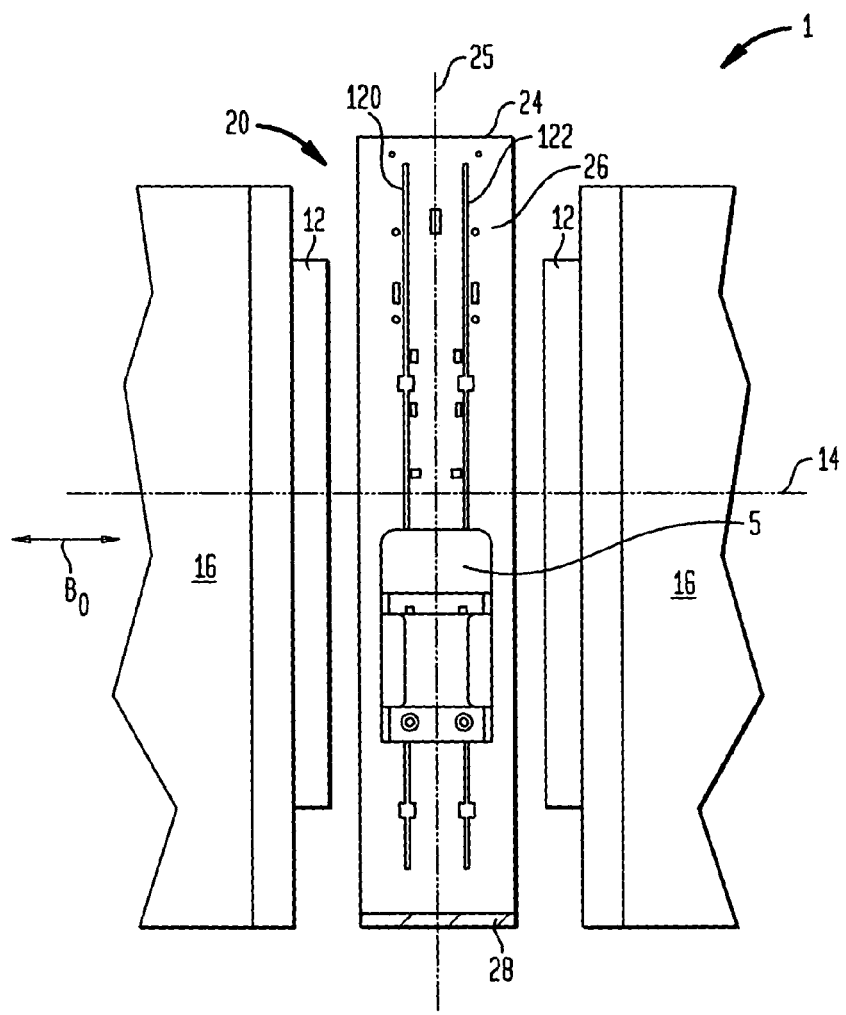
FIG. 1B is a front view of the system of FIG. 1A in accordance with an aspect of the present invention.

Turning to FIGS. 1A and 1B, there is illustrated a system 1 according to an aspect of the present invention. The system 1 includes a fixture 5 and a static field magnet having a frame 10 including a pair of poles 12 spaced apart from one another along a horizontal pole axis 14. Frame 10 further includes flux conducting and return members that, in the particular embodiment illustrated, include a pair of sidewalls 16 and columns 18 extending between the sidewalls 16. The particular frame depicted in FIGS. 1A and 1B is generally in accordance with the aforementioned U.S. Pat. No. 6,677,753, (hereinafter "the '753 patent") although other configurations may be employed. The opposed poles define a patient-receiving space or gap 20 between them. The magnet further includes a source of magnetic flux adapted to direct into and out of the gap through poles 12 so as to form a static magnetic field having a field vector $B_0$ in the horizontal direction, parallel to pole axis 14. In the particular embodiment illustrated, the flux source includes a pair of electromagnet coils 22 encircling poles 12. These coils may be superconductive or resistive coils. Alternate flux sources such as coils disposed at other locations along the ferromagnetic frame and permanent magnets also may be employed.

The apparatus further includes a patient support assembly including a bed or patient support 24 defining an elongated patient supporting surface 26 having a lengthwise axis 25 and a platform 28 projecting from the supporting surface at a foot end of the bed. In addition, a seat may be mounted to supporting surface 26 to allow a patient to be positioned in a sitting position (see, for example, FIGS. 6-9). The patient support assembly further includes a frame 30. Bed 24 is pivotably mounted to the frame 30 for movement about a generally horizontal pivot axis 32. Pivot axis 32 is substantially parallel to pole axis 14. Bed 24 can pivot between an upright position in which the lengthwise direction over the bed extends generally vertically as seen in FIG. 1 and a fully horizontal position, in which the lengthwise direction of the bed 24 extends horizontally. As further described in the '753 patent, bed 24 also may provide for vertical motion relative to frame 30 and hence relative to the static field magnet 10. Moreover, frame 30 can provide for horizontal movement relative to the static field magnet. Appropriate actuators and control devices (not shown) are provided for moving the bed and for moving support frame 30.

As seen in FIG. 1B, the patient receiving surface 26 includes a pair of slots 120 and 122 extending parallel to each other in the longitudinal direction 25 of the support 24. As shown in greater detail in FIG. 2, the slots 120 and 122 are generally T-shaped 124 in cross section. Thus, each slot has a narrow top portion 128 where the slots open to the surface 26 remote from the opening of the slot. Pockets 130 are provided in pairs along the lengths of the slots 120 and 122. These pockets are generally wider than the narrow top portion 128. The surface 26 further includes a pair of rectangular slots 132 disposed opposite each other along the lateral direction of the surface 26. In addition to the foregoing, commonly assigned U.S. patent application Ser. No. 10/131,843, the disclosure of which is hereby incorporated by reference, discloses additional methods for connecting structures to the support surface.

Figure 3:
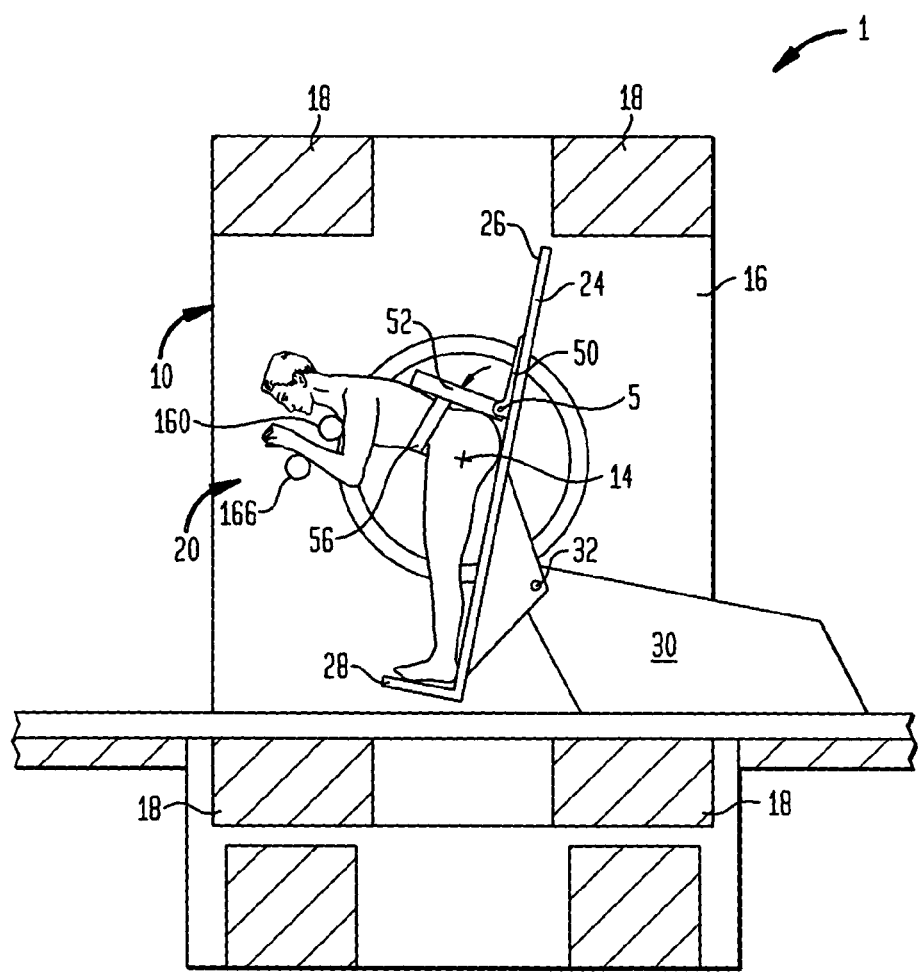
FIG. 3 illustrates a magnetic resonance imaging system in accordance with an aspect of the present invention.

As best seen in FIG. 3, the fixture 5 includes a base portion 50 and a slotted portion 52, which is preferably designed for receiving a planar coil antenna. The fixture further preferably includes a strap 56 that is securable around the waist area of the patient P, although, as discussed in further detail below, other embodiments need not include a strap. In accordance with an aspect of the present invention, as the patient P moves from a first position (e.g., standing upright) as shown in FIG. 1A to a second position (e.g., bent over) as shown in FIG. 3, the position of an antenna in the slotted portion 52 of the fixture 5 remains substantially fixed relative to the anterior surface of the patient P's anatomy and/or anatomical area of interest. Accordingly, the fixture 5 allows images of, for example, the spine to be taken in both positions with little or no sacrifice of the magnetic resonance signals that are received by an antenna housed in the slotted portion 52.

FIG. 4 illustrates various views of a fixture 400 in accordance with an aspect of the present invention. In particular, FIG. 4A illustrates a perspective view of a fixture 400 in accordance with an aspect of the present invention. The fixture 400 includes a base member 406 and an antenna holding member 410. The base member 406 is designed to be mounted or affixed to the support surface 26 of the support 24. In particular, the base member 406 includes a pair of locking knobs 412, which are used to secure the fixture 400 to the support 24. The base member further preferably includes a pair of rearward mounting members 414 (See FIG. 4B). The rearward mounting members 414 are preferably secured to the base member 406 using screws via openings 416. The rearward mounting members 414 also preferably include a neck portion 416 that is terminated on a head 418. The neck 416 and head 418 are desirably designed to be inserted into slots on the support surface 26 of bed 24 and therefore are preferably circular in shape. The shape of this member, however, may be changed to any shape that allows the mounting member 414 to be inserted into the slots on the support surface 26.

As discussed above with reference to FIG. 2, the support surface 26 preferably includes a pair of slots 120 and 122, which are generally T-shaped 124 in cross-section. Thus, each slot has a narrow top portion 128 where the slots open to the surface 26 remote from the opening of the slot. Pockets 130 are provided in pairs along the lengths of the slots 120 and 122. These pockets 130 are generally wider than the narrow top portion 128 and are conveniently located to allow the rearward mounted circular member 414 to be inserted into the slots 120 and 122. The surface 26 further preferably includes a pair of rectangular slots 132 disposed opposite each other along the lateral direction of the surface 26. Each pair of rectangular slots 132 are, conveniently located along the lateral direction to allow for insertion of the locking knobs 412 into the slots 120, 122.

In accordance with the foregoing discussion, the locking knobs 412 and rearward mounting circular members 414 allow the base member 406 of the fixture 400 to be mounted to the surface 26 of bed 24. In addition, the slots 120, 122 allow the fixture 400 to be conveniently positioned at various locations along the lengthwise axis 25 of the bed 24. Preferably, the locking knobs 412 and rearward mounting members 414 are inserted into the slots 120, 122 of the bed 24. Thereafter, the position of the fixture 400 is slidably adjusted along the direction of the lengthwise axis 25 to a preferred measurement position. Once at the preferred position, the fixture 400 is then locked into place using locking knobs 412. The patient's anatomy is then placed adjacent to the antenna holding member 410 so that imaging may be performed. In addition, although the fixture 400 is preferably mounted using member 414 and locking knobs 412, the fixture 400 may also be mounted using Velcro, suctions cups or other means that allow the fixture 400 to be adjusted to suit the size of the patient and allow the anatomical area of interest to be imaged.

Figure 4A:
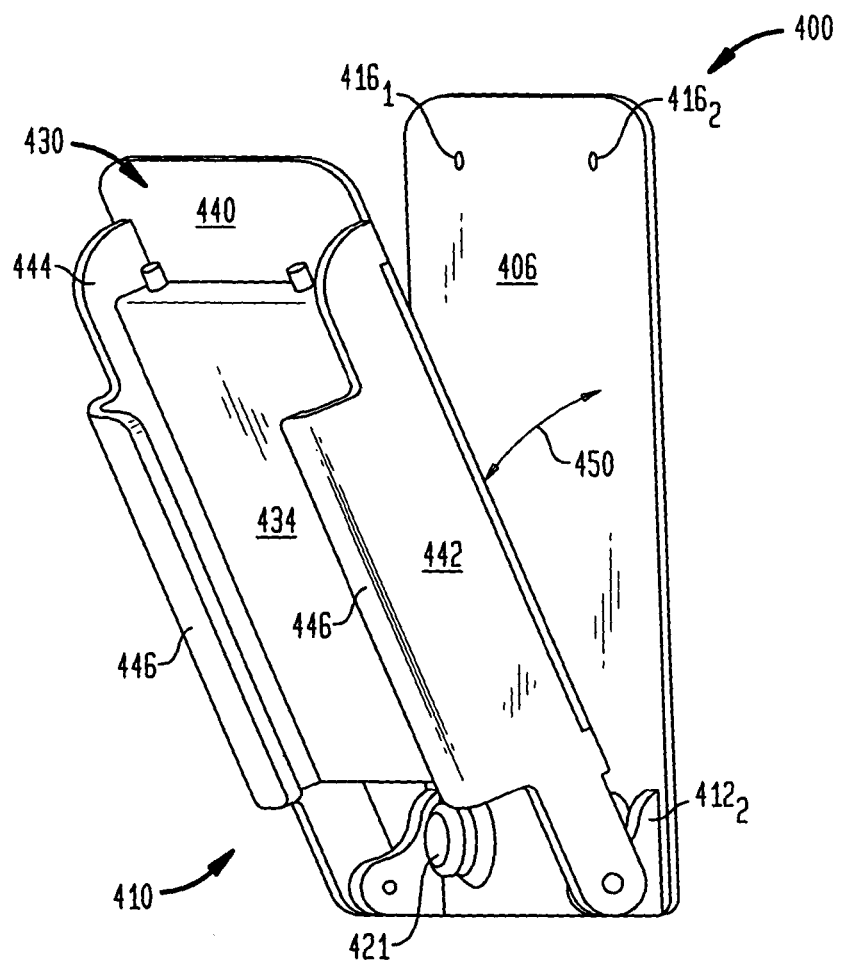
FIGS. 4A, 4B, and 4C illustratively depict different views of an apparatus in accordance with an aspect of the present invention.
Figure 4B:
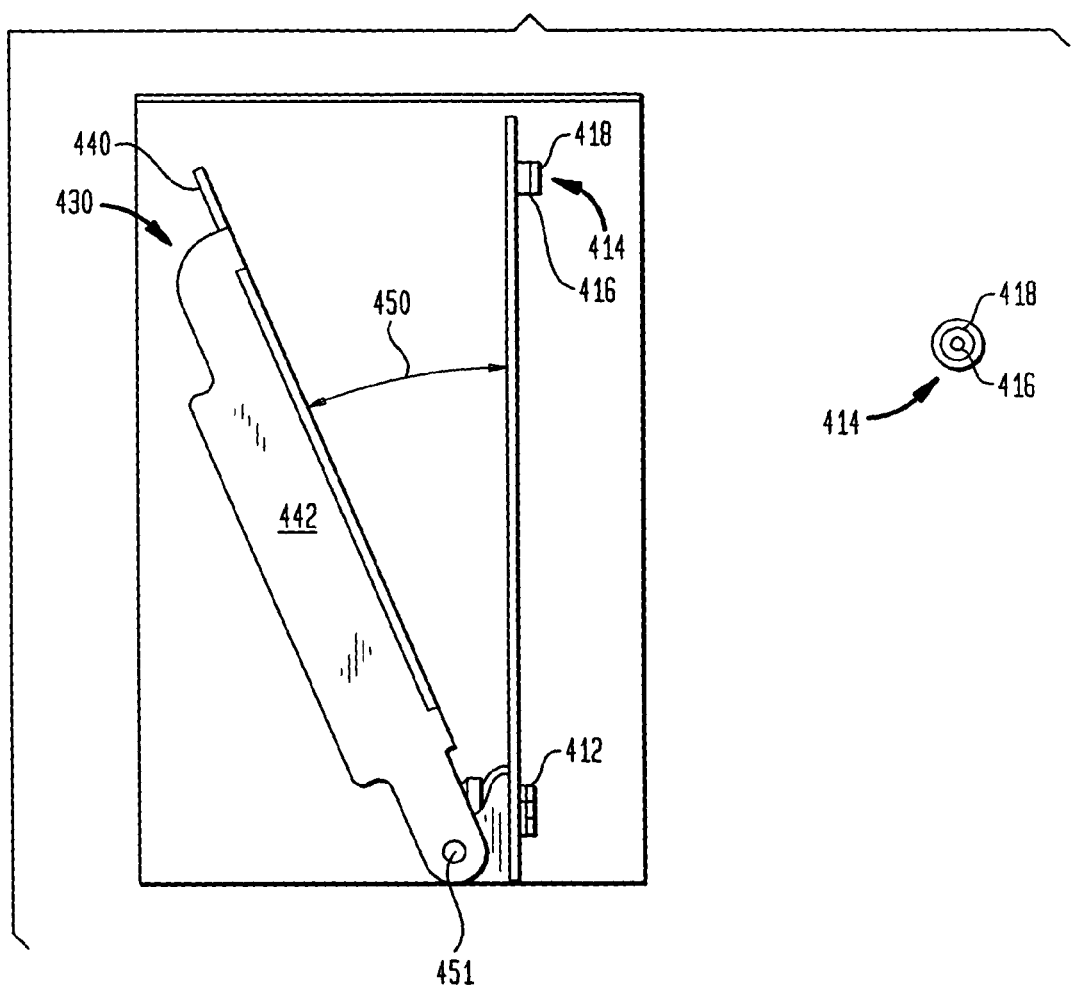
Figure 4C:
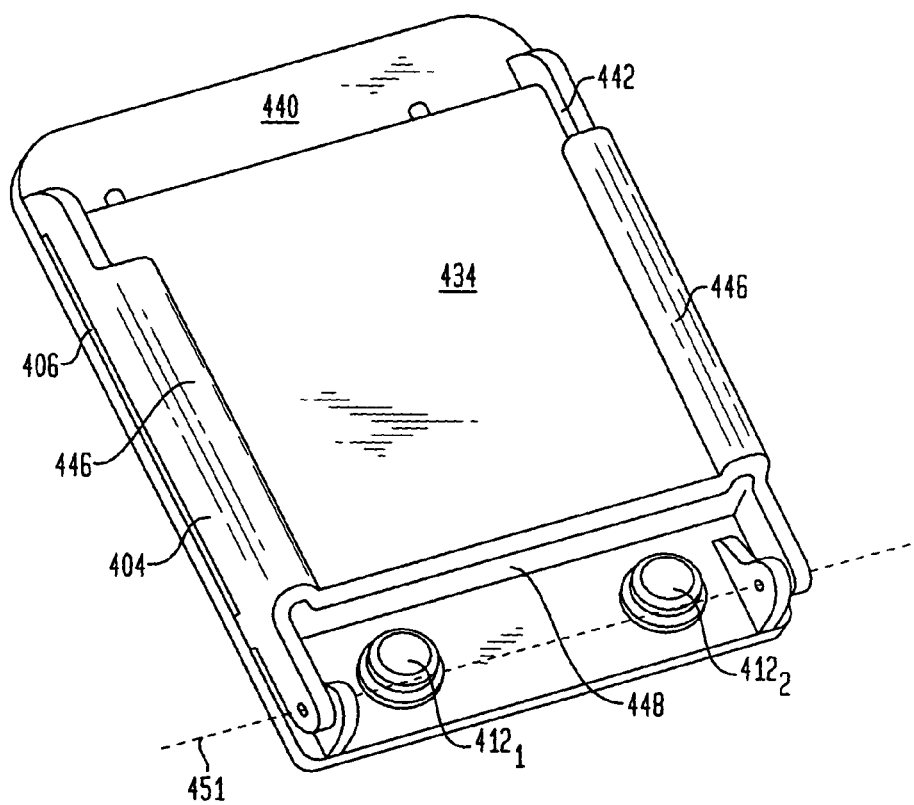

With reference to FIGS. 4A, 4B and 4C, the antenna holding member 410 comprises a base portion 440 having a substantially rectangular shape. A pair of sidewalls 442, 444 project from the base portion 440 to form the receiving pocket or slot 430. The distal end of each sidewall is terminated by a flange member 446 having a horizontal portion substantially parallel to the base portion 440. The holding member further includes a back wall 448. The flange members 446 and back wall 448 serve to hold an antenna 434 in the pocket or slot 430 as the holding member 410 rotates or moves to different positions during measurement.

As best seen in FIG. 4A and FIG. 4C, the antenna holding member 410 is preferably pivotably mounted to the base member 406. The holding member 410 may be mounted using any hinge that allows downward or upward rotation to and from the base member as shown by arrow 450. The arrow 450 illustrates an arc defined by the pivoting motion of the holding member 410 or antenna 434 about a pivot point or axis 451. In addition to using hinges, the holding member 410 may be mounted using a torsional spring that maintains the fixture in a locked position as shown in FIG. 4C. When a torsional spring is used, an operator or a patient may then unlock the spring so that the holding member extends from the base member as shown, for example, in FIG. 4A, thereby causing the holding member 410 to be forced against the surface of a patient P. Where a torsional spring is used, the spring is preferably made from a magnetically translucent material such as copper.

Figure 4D:
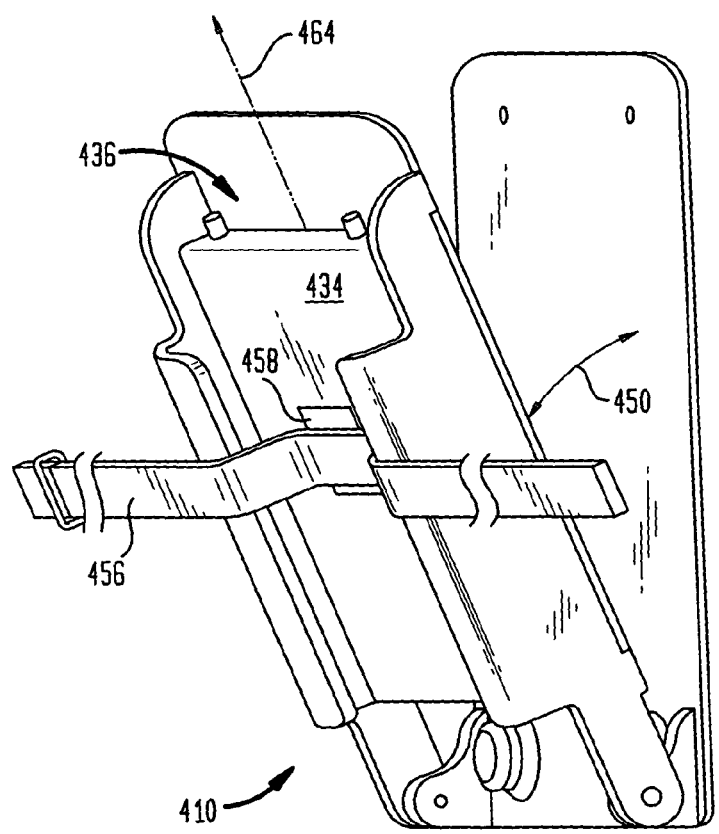
FIG. 4D illustrates an apparatus in accordance with an aspect of the present invention.

In lieu of or in addition to a torsional spring, the fixture 400 may be used or fitted with a strap, such as strap 56 shown in FIG. 3, that aids in maintaining the position of antenna 434 relative to the imaging area of anatomical interest. As best seen in FIG. 4D, a strap 456 is preferably attached to antenna 434 using Velcro. In particular, the antenna 434 is equipped with a mating portion of Velcro strip 458, which mates with the strap 456. The size of the strip 458 may vary and may cover as much of the facing surface area of the antenna 434 as desired. Preferably, a patient is fitted with strap 456 prior to entering the receiving space of the magnet. Once the strap 456 is appropriately secured to the patient, the patient then enters the receiving space of the magnet and is positioned so that the strap 456 mates with the strip 458. In accordance with this aspect of the present invention, as the patient changes position so that the holding member 410 pivots along direction 450, the antenna 434 translates substantially linearly along the direction 464. In this way, the position of an antenna in the slot 430 stays fixed relative to the portion of the patient's anatomy that is being imaged.

Alternatively, a patient may be fitted with the strap after entering the receiving space and positioned adjacent to the fixture. In this regard, the strap may be attached to the fixture and then fitted to the patient. As such, the strap may also be threaded through slots (not shown) formed in sidewalls 442, 446.

As discussed the holding member 410 preferably includes a receiving pocket or slot 430 that advantageously allows the position of an antenna in the slot 430 to translate linearly as the holding member 410 pivots about the base 406. Although the holding member 410 has been generally described above as including a receiving pocket or slot 430, the holding member may also comprise a rectangular, square, circular or appropriately shaped box for housing a receiving coil or antenna that is used as part of the imaging process.

Figure 5A:
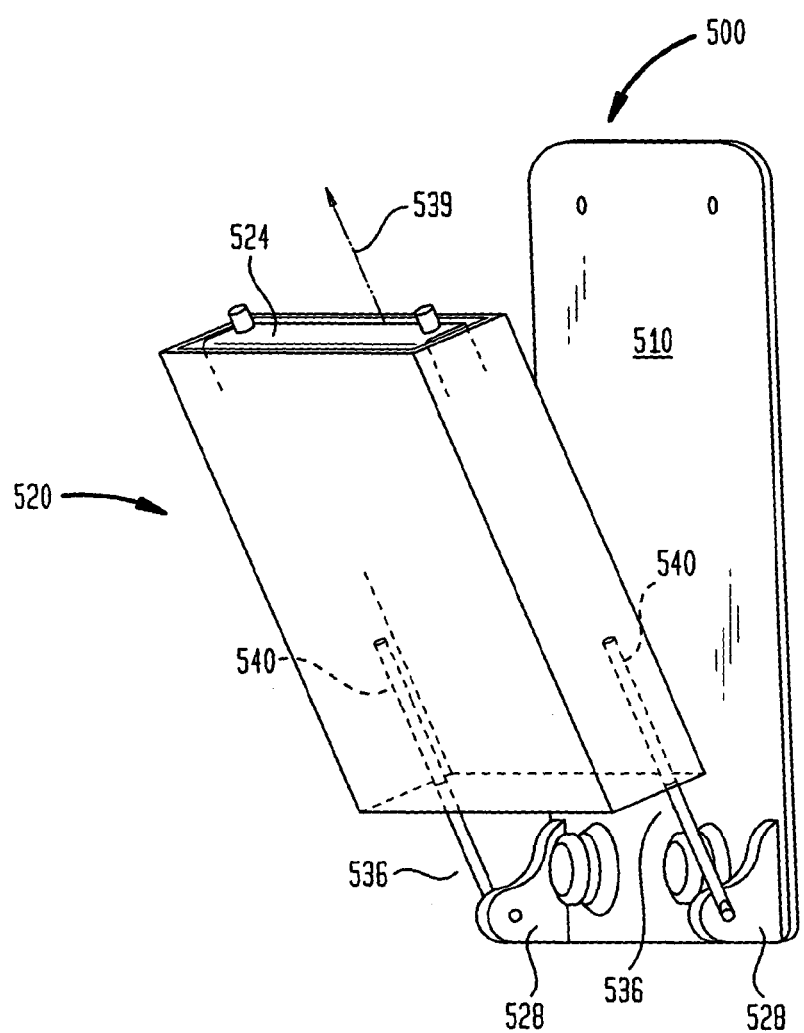
FIG. 5A illustrates an apparatus in accordance with an aspect of the present invention.

In particular, a fixture 500 in accordance with an aspect of the present invention is as shown in FIG. 5A. The fixture 500 comprises a base portion 510 and a holding member 520. The base member 510 is preferably adapted to be mounted to a bed or patient support, such as bed 24 for example. The base member 510 may, therefore, be implemented as discussed above for base member 406.

The holding member 520 comprises a box-like structure for receiving an antenna 524. The holding member 520 is pivotably or rotatably mounted to the base 510 via support members 528 that project from the base 510 and rods 536 associated with the holding member 520. Rods 536 comprise guide rods that allow the holding member 520 to translate linearly along direction 539 as the rods 536 pivot about the support members 528. In particular, rods 536 are mounted to the holding member 520 through openings 540 such that the rods translate linearly in the openings 540 as the rods pivot about the support members 528. The rods 536 may comprise a cylindrical rod or pistons. The rods may also comprise rectangular or other shape slides that perform a similar function. The rods may also comprise a plurality of cylindrical or rectangular members arranged to telescope as the holding member pivots toward and from the base member 510. In this regard, such cylindrical members may be arranged so that the rod 536 is external to holding member 520. Alternatively, such cylindrical members may be arranged to telescope into and out of the openings 540. As discussed in relation to FIG. 4, the outer surface of the holding member 520 that is usually adjacent the patient's posterior surface may be affixed with Velcro for receiving a strap worn by a patient to aid in linearly translating the holding member 520.

Figure 5B:
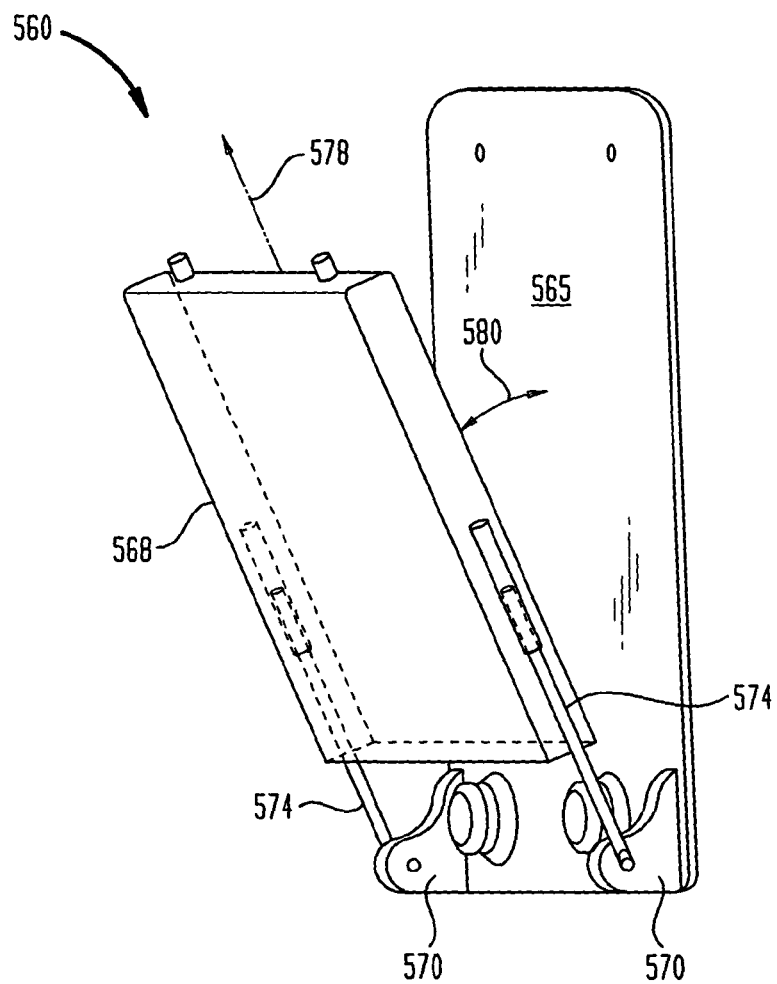
FIG. 5B illustrates an apparatus in accordance with an aspect of the present invention.

Turning now to FIG. 5B, there is illustrated a fixture or apparatus 560 in accordance with an aspect of the present invention. The apparatus 560 includes a base 565 as described above in relation to base members 510 or 406. The apparatus 560 further includes an antenna 568 that is pivotably mounted to the base 565 at support members 570. In particular, the apparatus 560 is mounted using rods 574. The rods 574 allow the antenna 568 to translate linearly or slide out along direction 578 as the antenna pivots or rotates. The rods 574 may comprise pistons that retract and extend as the antenna rotates toward and away from the base 565, i.e., along direction 580. The antenna 568 may be equipped with a strip of Velcro for mating with a belt or strap worn by a patient. In accordance with this aspect of the present invention, the antenna 568 is not enclosed in a fixture. Instead, the antenna is directly attached to the base 565. As such, the antenna may take any desired shape or size. For example, the antenna may be designed to cover a larger surface area or be circular in shape.

Figure 6:
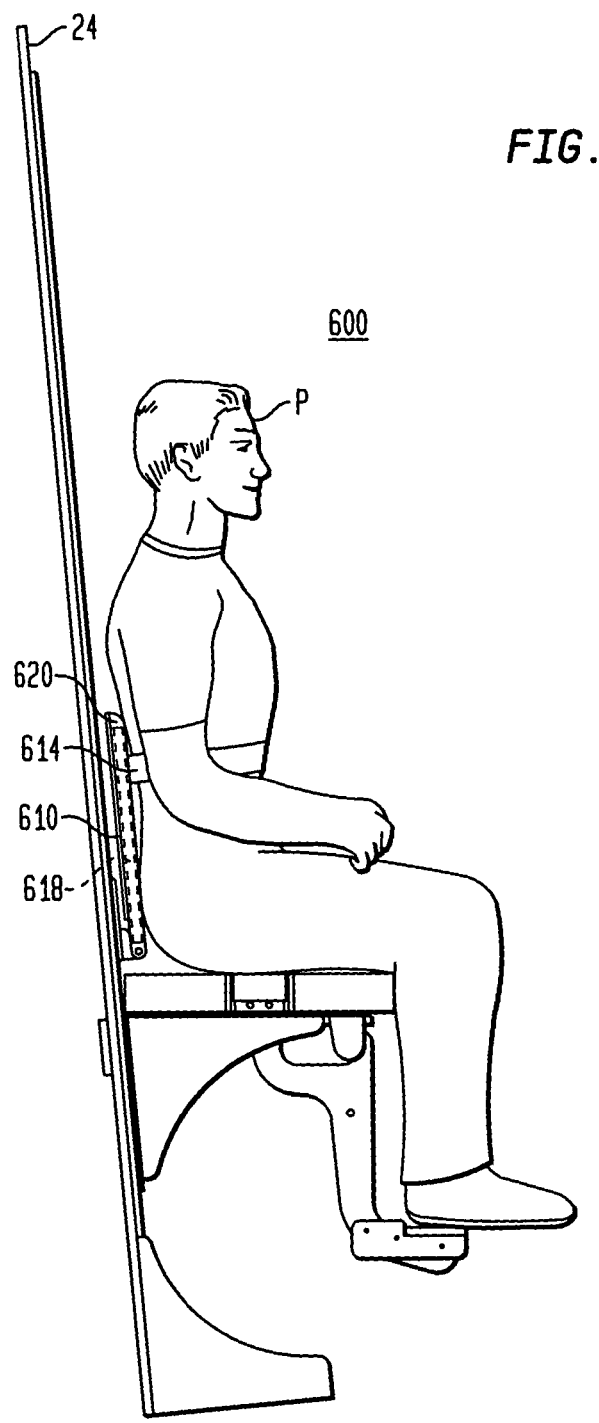
FIG. 6 illustratively depicts an MRI imaging system in accordance with an aspect of the present invention.
Figure 7:
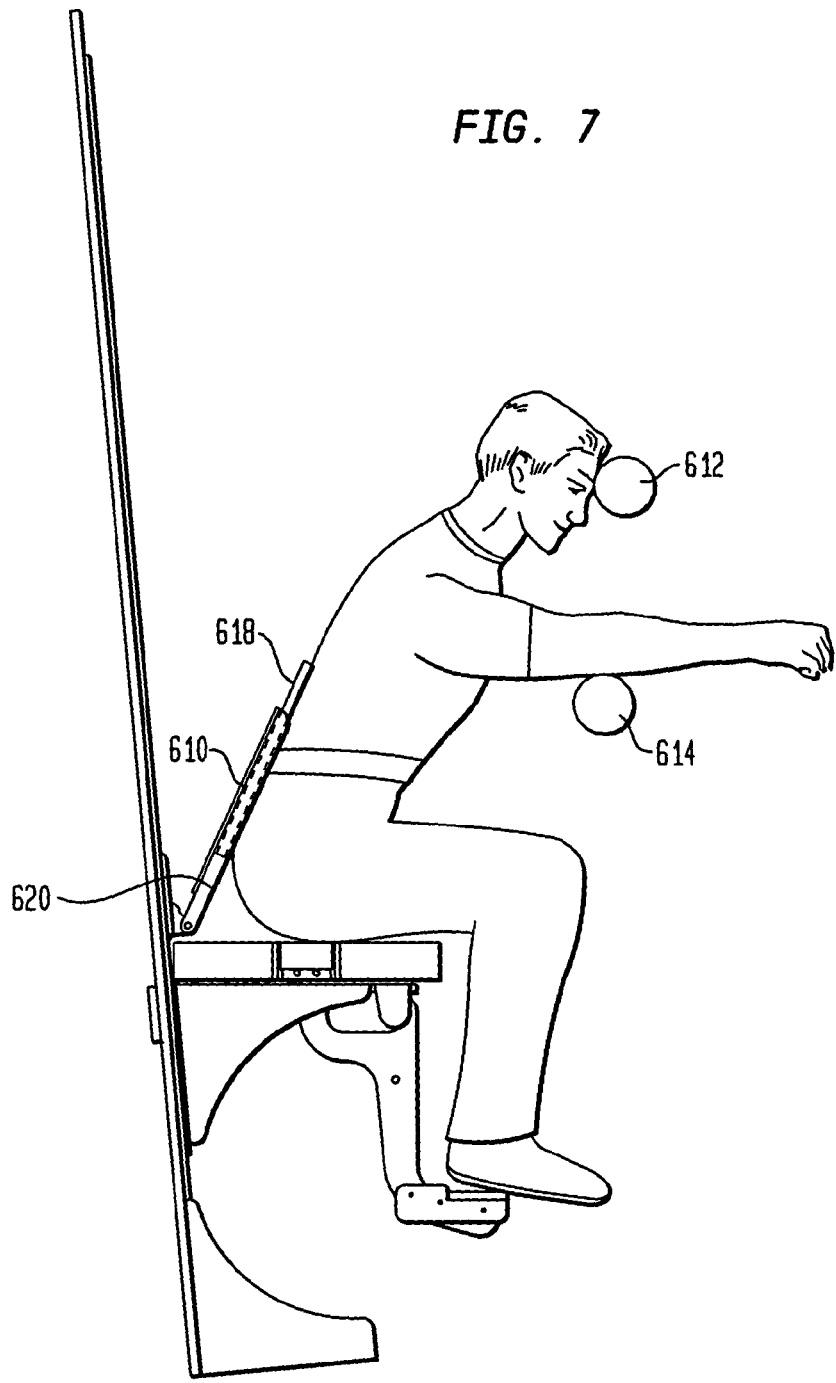
FIG. 7 illustratively depicts an MRI imaging system in accordance with an aspect of the present invention.

FIG. 6 illustrates an MRI imaging system in accordance with an aspect of the present invention. As shown in FIG. 6, the system 600 includes a bed, such as bed 24, to which is mounted a fixture 610. The fixture 610 is preferably implemented in accordance with the fixture shown in FIG. 4 and may also be implemented in accordance with FIG. 5. In addition, the fixture 610 includes a strap 614 for securing an antenna 618 in a holding portion 620 to the patient P. The patient P is oriented in an upright sitting position. In this position, magnetic resonance images of the patients lower lumbar region are preferably obtained. The patient may then be oriented in a second position as shown in FIG. 7. The patient's lower lumbar or spinal area may then be imaged in this second position. As shown in FIG. 7, as the patient leans forward in a flexed or flexion position, the antenna 618 preferably translates linearly along the longitudinal direction of the holding portion 620. In accordance with this aspect of the present invention, the fixture 610 maintains the antenna in a substantially fixed position relative to the anterior surface of the patient's anatomy and the portion of the patient's anatomy that is being imaged, in this case the spine, at two or more positions. In this way, images of the patient's spine may be obtained during kinetic maneuvers without significantly sacrificing the received signal strength of the magnetic resonance signals. The imaging information obtained in both positions may allow for quicker and more accurate determination of a patient's condition.

Figure 2:
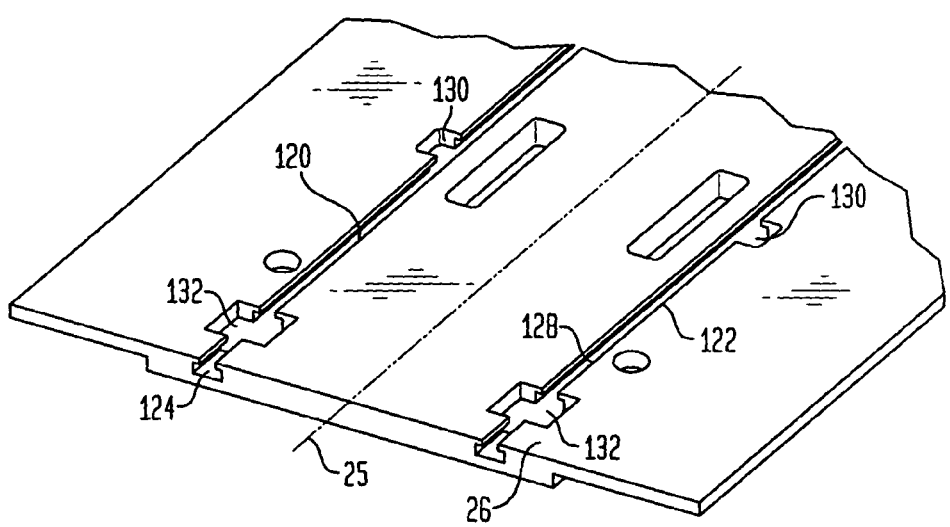
FIG. 2 is a partial exploded view of a portion of the support 24 in accordance with an aspect of the present invention.

As shown in FIG. 7, when the patient is leaning forward as shown, a pair of rest or support members 612, 614 are preferably provided to allow the patient to maintain a desired position, similar support members 160, 166 are also used in FIG. 2 for maintaining the patient in the desired position. The support members 612, 614 or 160, 166 may be implemented in accordance with commonly assigned U.S. application Ser. No. 10/694,693, the disclosure of which is incorporated by reference herein in its entirety. The support members are desirable, as they allow a patient to remain still when leaning forward. FIG. 2, in contrast to FIG. 7, shows the patient bent over in a standing position. In addition to the positions shown in FIGS. 3, 6 and 7, the patient may also be oriented between a fully upright standing or seated position, e.g., neutral position, and a bent over position, i.e., leaning forward or bent over partially or as far as possible.

Figure 8:
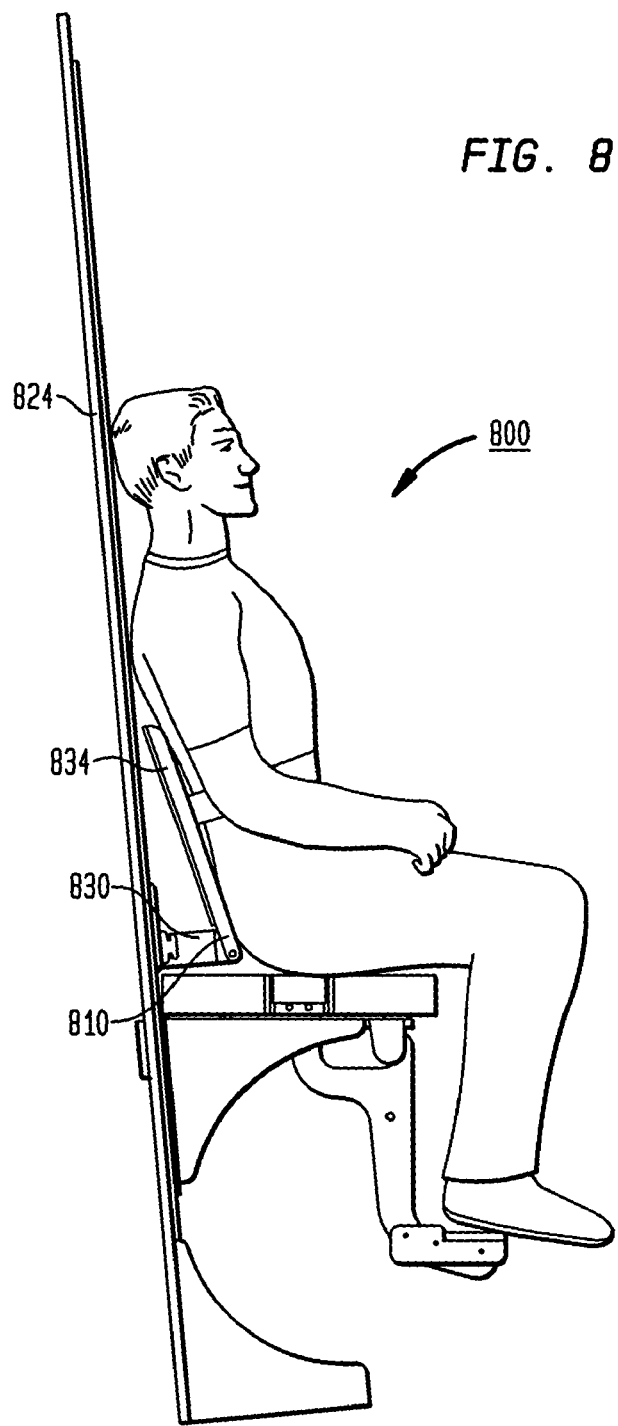
FIG. 8 illustratively depicts an MRI imaging system in accordance with an aspect of the present invention.

Turning now to FIG. 8, there is shown a system 800 in accordance with an aspect of the present invention. The system 800 includes a fixture 810 mounted to a bed 824. The fixture 810 preferably includes an elongated hinge support member 830 to which is mounted an antenna holder 834. The fixture 810 desirably allows the patient P to be oriented in an extended position, as shown, for imaging. In the extended position, the patient is preferably reclined at an angle relative to the fully upright seated position, which preferably allows the patient's spine to be extended for imaging. The patient may also be oriented such that the lower lumbar area is arched in the extension position. In accordance with the fixture 810 shown in FIG. 8, the patient may be imaged in the extended position shown, as well as a leaning forward position and the arched (or extension) position (with or without support members 612, 614). As discussed above, different positions during imaging will typically yield different imaging results.

The positions shown and discussed above allow for dynamic kinetic studies of various areas of the anatomy. Such studies tend to yield additional information that assist in the diagnosis of conditions that may be affecting a patient. The different positions may, for example, yield clearer images of the anatomical area of interest than currently available by systems that do not provide the foregoing positional flexibility and fixtures.

As described above, the fixture may include a strap and/or a torsional spring. In the preferred embodiment, only a strap is necessary. Nevertheless, the strap and torsional spring, if used together, may improve maintaining the fixture close to the patient's anatomy as the patient is oriented in different positions during imaging. Furthermore, although the torsional spring is disclosed and preferably being made of copper, the spring may be made from other translucent materials including phosphor bronze, beryllium copper and 300 series stainless steel.

Figure 9:
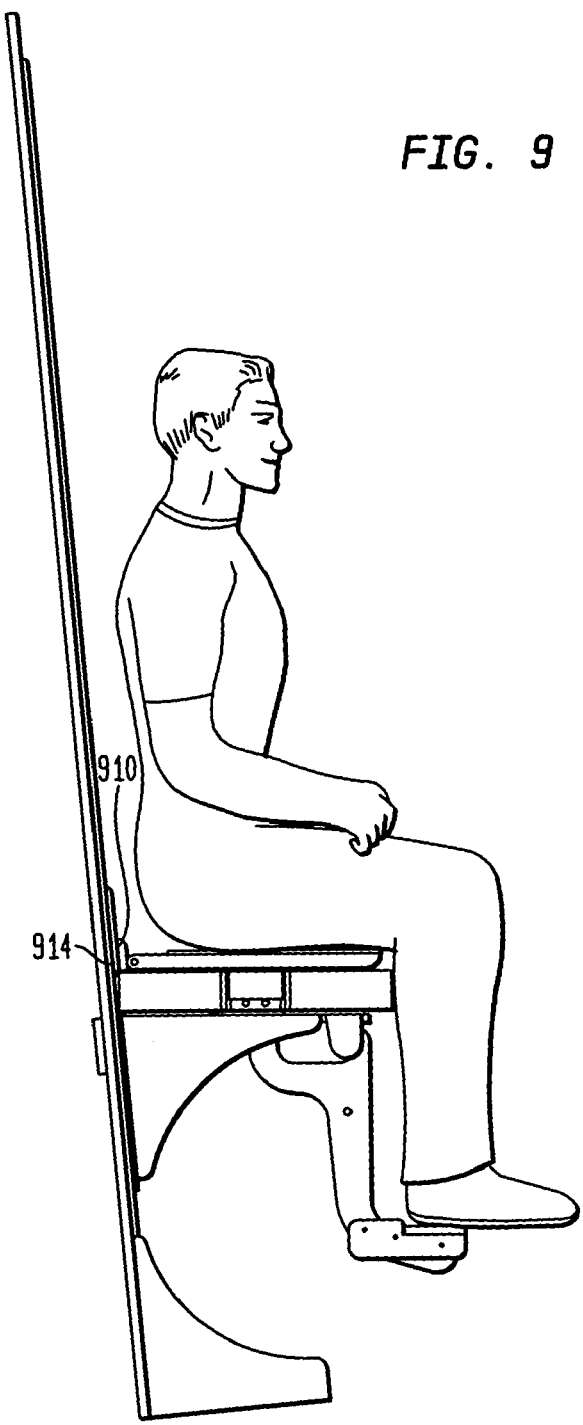
FIG. 9 illustratively depicts an MRI imaging system in accordance with an aspect of the present invention.

Turning now to FIG. 9, there is shown an additional aspect of the present invention. In FIG. 9, a fixture 910, which may be implemented in accordance with FIG. 4, is shown in a position that allows a patient to sit on the antenna holder 914. In accordance with this aspect of the present invention, imaging of the prostate or the pelvic region may be performed using the fixture 910.

In the foregoing discussions, the system is depicted as comprising a static field magnet that includes a pair of poles and a frame that act as a flux return member. The fixture, however, in accordance with the various aspects of the present invention, may be used in any horizontal field magnet that allows a patient to be oriented in the positions described herein. For example, the system may include one or more superconducting coils arranged to provide a static magnetic field across a gap into which a patient may be positioned. Alternatively, the superconducting magnet may include poles without a ferromagnetic frame. A patient may then be placed in the gap in a chair or other patient positioning devices, or may stand in the gap. The patient may then be preferably imaged in accordance with the various aspects of the present invention described above.

In addition, although the invention has been generally described with respect to imaging the lumbar region and spine, it should be understood that the invention may also be used in obtaining images of thoracic and cervical spine.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for magnetic resonance imaging, comprising:
a magnetic resonance imaging apparatus having a receiving space for positioning a patient;
an elongated patient support device for receiving the patient and that is positionable in the receiving space; and
a fixture having a housing including a slot for receiving an antenna such that the position of a portion of the patient's anatomy to be imaged remains fixed relative to the antenna as the patient moves between a first position and a second position, the antenna having a strap for receiving the patient, wherein the antenna and the housing pivot from a first antenna position to a second antenna position about a pivot axis relative to the elongated patient support surface, and wherein the slot allows the position of the antenna to translate linearly in a first direction relative to the housing as the housing and the antenna pivot from the first antenna position to the second antenna position about the pivot axis, and wherein the strap is configured to aid in maintaining the position of the antenna relative to the portion of the patient's anatomy as the housing and the antenna pivot from the first antenna position to the second antenna position about the pivot axis, and wherein the first direction is perpendicular to the pivot axis.

2. The system of claim 1, wherein said fixture is mounted to said patient support and the portion of the patient's anatomy to be imaged comprises the lumbar spine.

3. The system of claim 2, wherein the first position is an erect lumbar position.

4. The system of claim 2, wherein the second position is a flexion lumbar position.

5. The system of claim 2, wherein the second lumbar position is an extended lumbar position.

6. The system of claim 2, wherein the second position is an extension lumbar position.

7. The system of claim 1, wherein said fixture comprises a base portion and the housing is pivotably mounted to said base portion, said base portion being mounted to said patient support so as to allow an antenna positioned in said antenna receiving slot to remain fixed relative to the patient's anatomy as the patient moves between the first position and the second position.

8. The system of claim 1, wherein the strap includes a portion that comprises a Velcro strip that is mateable with another portion of Velcro strip on said antenna.

9. The system of claim 1, wherein said antenna receiving portion further includes one or more slots for receiving the strap.

10. The system of claim 7, wherein said base portion is pivotably mounted to the housing by a pair of torsional spring members, wherein each torsional spring member applies a force to secure the antenna holder against the patient.

11. The method of claim 10, wherein said pair of torsional spring members are made from a magnetically translucent material.

12. The system of claim 11, wherein the magnetically translucent material is selected from the group consisting of beryllium copper, phosphor bronze and 300 series stainless steel.

13. The system of claim 2, wherein the patient is positioned in a sitting position.

14. The system of claim 2, wherein the patient is positioned in a standing position.

15. A method for performing magnetic resonance imaging, comprising:
providing a magnetic resonance imaging apparatus having a patient receiving space and an elongated patient support device located within the patient receiving space;
mounting a fixture having a housing including a slot for receiving an antenna, the antenna having a strap for receiving the patient;
positioning a patient in the patient receiving space such that a surface of the patient's anatomy is adjacent to the fixture; and
acquiring magnetic resonance images of a portion of the patient's anatomy with the patient oriented in a first position and a second position such that the position of the patient's surface adjacent the housing remains fixed relative to the antenna during movement between the first and second positions, wherein the housing and antenna rotate from a first antenna position to a second antenna position about an axis of rotation relative to the elongated patient support device, wherein the slot allows the position of the antenna to translate linearly in a first direction relative to the housing as the housing and antenna pivot from the first antenna position to the second antenna position about the pivot axis, wherein the strap is configured to aid in maintaining the position of the antenna relative to the surface of the patient's anatomy as the housing and the antenna pivot from the first antenna position to the second antenna position about the pivot axis, wherein the first direction remains perpendicular relative to the pivot axis as the housing and the antenna pivot from the first antenna position to the second antenna position about the pivot axis.

16. The method of claim 15, wherein positioning the patient comprises positioning the patient in a sitting position.

17. The method of claim 15, wherein positioning the patient comprises positioning the patient in a standing position.

18. The method of claim 15, wherein in the first position the patient's lumbar region is positioned adjacent to the fixture and oriented in the extension position.

19. The method of claim 15, wherein in the first position the patient's lumbar region is positioned adjacent to the fixture and oriented in a neutrally upright position.

20. The method of claim 15, wherein in the second position the patient's lumbar region is positioned adjacent to the fixture and oriented in a flexion position.

21. A method for performing dynamic kinetic studies of the spine comprising:
providing magnetic resonance imaging apparatus having a gap and a static horizontal magnetic field within the gap;
positioning an elongated patient support device in the gap of the apparatus;
equipping the elongated patient support device with a fixture having a housing including a slot for receiving a radio frequency coil, the radio frequency coil having a strap for receiving the patient;
positioning the patient next to the elongated patient support device such that a portion of the patient's lumbar region is proximate the fixture;
acquiring a first magnetic resonance image of the patient's lumbar region in a first position;
orienting the patient in a second position relative to the first position such that the portion of the patient's lumbar region proximate the radio frequency coil remains fixed relative to the radio frequency coil between the first position and the second position, wherein the radio frequency coil and the housing pivot from a first radio frequency coil position to a second radio frequency coil position about a pivot axis relative to the elongated patient support device, and wherein the slot allows the position of the antenna to translate linearly in a first direction relative to the housing as the housing and the radio frequency coil pivot from the first radio frequency coil position to the second radio frequency coil position about the pivot axis, wherein the strap is configured to aid in maintaining the position of the radio frequency coil relative to the portion of the patient's lumbar region as the housing and the radio frequency coil pivot from the first radio frequency coil position to the second radio frequency coil position about the pivot axis, and wherein the first direction is perpendicular to the pivot axis; and
acquiring a second magnetic resonance image of the patient's lumbar region in the second position.

22. The method of claim 21, wherein the first position comprises an upright neutral position.

23. The method of claim 22, wherein the second position comprises a flexion position.

24. The method of claim 22, wherein the second position comprises an extension position.

25. An apparatus for use in a magnetic resonance imaging system, comprising:
a base;
an elongated patient support surface; and
an antenna holder including a slot for receiving a coil antenna pivotably mounted to the base such that as a patient moves from a first position to a second position, the position of the patient's anatomy adjacent an antenna associated with the antenna holder remains fixed relative to the antenna, the antenna having a strap for receiving the patient; and
wherein the antenna and antenna holder pivot from a first antenna position to a second antenna position about a pivot axis relative to the elongated patient support surface and the slot allows the position of the antenna to translate linearly in a first direction relative to the holder as the holder and the antenna pivot from the first antenna position to the second antenna position about the pivot axis, and wherein the strap is configured to aid in maintaining the position of the antenna relative to the patient's anatomy adjacent the antenna as the housing and the antenna pivot from the first antenna position to the second antenna position about the pivot axis, wherein the first direction remains perpendicular relative to the pivot axis as the holder and the antenna pivot from the first antenna position to the second antenna position about the pivot axis.

26. The apparatus of claim 25, wherein the slot comprises a base, a pair of sidewalls projecting from the base and a rear wall projecting from the base between the pair of sidewalls.

27. The apparatus of claim 26, wherein the antenna comprises a planar coil antenna.

28. The apparatus of claim 25, wherein the antenna holder is pivotably mounted to the base using a torsional spring, wherein the torsional spring applies a force to secure the antenna holder against the patient.

\* \* \* \* \*